United States Patent [19]

Fujiwara et al.

[11] 4,336,332

[45] Jun. 22, 1982

[54] PROCESS FOR THE MANUFACTURE OF HYDROXYLATED STEROIDS

[75] Inventors: Mitsuhiko Fujiwara; Akiko Fujiwara, both of Kamakura; Chikara Miyamoto, Yokohama, all of Japan

[73] Assignee: Hoffmann-La Roche, Inc., Nutley, N.J.

[21] Appl. No.: 118,282

[22] Filed: Feb. 4, 1980

[30] Foreign Application Priority Data

Feb. 20, 1979 [CH] Switzerland ............................ 1675/79

[51] Int. Cl.³ ............................................. C12P 33/06
[52] U.S. Cl. ....................................... 435/58; 435/911
[58] Field of Search .......................................... 435/58

[56] References Cited

U.S. PATENT DOCUMENTS 2,960,436 11/1960 Thoma et al. .......................... 435/58
2,960,513 11/1960 Thoma et al. .......................... 435/58
2,962,512 11/1960 Bernstein et al. ...................... 435/58
3,047,470 7/1962 Pruess et al. .......................... 435/60
3,880,895 4/1975 Greenspan et al. ................... 435/58

OTHER PUBLICATIONS

Chemical Abstracts, vol. 75, 72841W (1971).
Biochem Biophys. Acta 239, pp. 103–110 (1971).

Primary Examiner—Alvin E. Tanenholtz
Attorney, Agent, or Firm—Jon S. Saxe; George M. Gould; John B. Wilson

[57] ABSTRACT

The invention relates to a process for producing $7_\alpha$-hydroxylated steroids by fermenting or reacting a steroid to be hydroxylated with microorganisms of the genus Botryodiplodia or enzyme extracts thereof until hydroxylation occurs. The invention process produces steroid compounds which are pharmacologically valuable substances.

4 Claims, No Drawings

PROCESS FOR THE MANUFACTURE OF HYDROXYLATED STEROIDS

BACKGROUND OF THE INVENTION

The microbiological 7α-hydroxylation of steroids by means, for example, of Mucor griseocyanus is known and described in Canadian Journal of Microbiology, Vol. 13, pages 1271-1281 (1967). It has now surprisingly been found that a 7α-hydroxylation of steroids can be carried out with microorganisms of the genus Botryodiplodia, which are entirely different from Mucor griseocyanus.

SUMMARY OF THE INVENTION

The invention relates in its preferred embodiment to a process for the manufacture of 7α-hydroxylated steroids by fermentation of 7-unsubstituted steroids of the pregnane or androstane series with microorganisms of the genus Botryodiplodia or by reaction with enzyme extracts thereof. The invention process produces steroid compounds which are intermediates for the manufacture of pharmacologically valuable substances and which themselves exhibit pharmacological (e.g. hormonal) activity.

DETAILED DESCRIPTION OF THE INVENTION

The present invention relates to a process for producing hydroxylated steroids comprising fermenting a steroid to be hydroxylated with microorganisms of the genus Botryodiplodia in a culture solution or medium until the steroid to be hydroxylated is hydroxylated. The invention process also includes a process for producing hydroxylated steroids comprising reacting the steroid to be hydroxylated with a hydroxylating enzyme extract obtained from the microorganisms of genus Botryodiplodia in a reaction mixture until the steroid to be hydroxylated is hydroxylated.

More particularly, in a preferred embodiment of the invention, the steroids to be hydroxylated (starting compounds) have been selected from dehydroepiandrosterone, pregnenolone or steroids of the formula

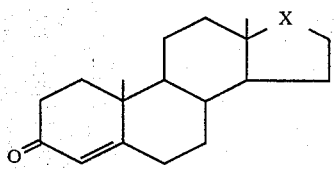

wherein X represents the following groups:

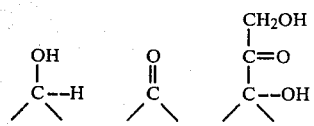

With the use of compounds of formula I as the steroid to be hydroxylated (the starting material) in the invention process, there are obtained hydroxylated steroid compounds of following formula II:

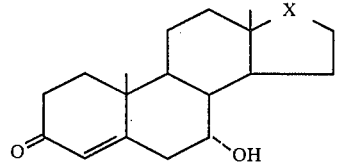

Wherein X has the aforementioned significance.

In the case of the fermentation of dehydroepiandrosterone by the invention process there are obtained 7α-hydroxy-4-androstene-3,17-dione and 7α,17β-dihydroxy-4-androsten-3-one; in the case of the fermentation of pregnenolone there is obtained the 7α-hydroxy-progesterone.

Any strain of the microorganisms of the genus Botryodiplodia capable of the 7α-hydroxylation of steroids; especially such steroids of the formula I, alone with pregnenolone and dehydroepiandrosterone, as well as variants thereof, can be used in the invention process. Preferred strains are, for example, IFO 6469 and Botryodiplodia malorum CBS 134.50.

The microorganisms can be used in the form of mycelium in a culture medium or solution, or an hydroxylating enzyme extract can be produced from the microorganisms by any process recognized in the art for this purpose and can be used to carry out the invention process. A suitable culture solution or medium can be manufactured and inoculated with the microorganism. Suitable culture solution or media are such ones which contain carbon sources, nitrogen sources, inorganic salts and other nutrient substances permitting the growth of the microorganism. The preferred carbon sources are, for example, glucose, saccharose, dextrin, mannose, starch, lactose and glycerine; nitrogen sources are, for example, nitrogen-containing organic substances such as peptone, meat extract, yeast extract, cornsteep liquor and casein, or nitrogen-containing inorganic compounds such as nitrates and inorganic ammonium salts; organic salt sources are, for example, phosphates or sodium, potassium, magnesium, manganese, iron and copper salts.

In the cultivation of the microorganism, the microorganism can be submersed in the culture, as by shaking the culture, or the microorganism may be cultivated in a stationary culture. The microorganism is preferably cultivated under aerobic conditions. Any art recognized procedure for cultivating the microorganism may be used.

The invention process is conveniently carried out by adding the steroid to be hydroxylated, such as the compound of general formula I, as a substrate to the cultivated microorganisms in the culture solution. The concentration of the substrate is not particularly significant but a concentration of 0.1 g per liter to 20 g per liter of medium is preferred. The hydroxylation in accordance with the invention process can be carried out by continuation of the cultivation of the microorganism under the above mentioned conditions in the presence of the steroid to be hydroxylated. The fermentation time needed for significant hydroxylation can vary depending on species and strain of the microorganism used, on the composition of the culture medium, on the substrate used and on the concentration of substrate and microorganism. In general, a fermentation time of 1-10 days suffices. The fermentation temperature preferred generally lies between 20° and 30° C., and a preferable pH between 4–9.

The substrate can be added to the culture of the microorganism during the cultivation of the microorganism or to the culture medium prior to sterilisation or prior to the inoculation with the microorganisms.

The hydroxylation in accordance with the invention can also be carried out with the mycelium of the microorganism isolated from the culture solution or with an enzyme extract manufactured from the cultivated microorganisms or the mycelium in a manner well known in the arts. In this case, the 7α-hydroxylation is conveniently carried out in aqueous solution, e.g. a buffer solution, in physiological salt solution, in fresh nutrient solution or in water.

The substrate (the steroid to be hydroxylated) can be added to the culture solution or aqueous solution in solid form or as a solution in a hydrophilic solvent such as acetone, dimethyl sulphoxide, methanol, ethanol, ethyleneglycol, propyleneglycol or dioxan. A surface-active agent or a dispersion agent can also be added to an aqueous suspension of the substrate, or the substrate can be emulsified by treatment with ultrasonic wave.

By means of the invention process, from 17α,21-dihydroxy-4-pregnene-3,20-dione and 17α-hydroxy-4-androsten-3-one there are obtained the corresponding 7α-hydroxylated steroids, i.e. 7α,17α,21-trihydroxy-4-pregnene-3,20-dione and 7α,17β-dihydroxy-4-androsten-3-one, respectively.

The fermentation product (the hydroxylated steroid) can be isolated from the fermentation mixture by any process recognized in the art for this purpose as, for example, by solvent extraction with an organic solvent which is not miscible with water, such as chloroform, methylene chloride or methyl acetate or by chromatography on carriers such as aluminum oxide, silica gel or cellulose. The fermentation product can also be purified by recrystallisation, e.g. from ethyl acetate, benzene or acetone.

With the use of 4-androstene-3,17-dione as the starting material there is obtained a mixture of 7α-hydroxy-4-androstene-3,17-dione and 7α,17β-dihydroxy-4-androstene-3-one. This mixture can be readily separated by chromatography, whereby one varies the polarity of the elution agent.

The hydroxylating microorganisms used according to the present invention include all strains belonging to the genus Botryodiplodia which are capable of hydroxylation as well as mutants and variants thereof. Particularly preferred strains are IFO 6469 and Botryodiplodia malorum CBS 134.50. A subculture of IFO 6469 has been deposited at Northern Regional Research Laboratory of the U.S. Department of Agriculture, Peoria, Ill., under NRRL No. 11174 and can be obtained therefrom. Cultures of B. malorum CBS 134.50 were obtained from Centraal-Bureau voor Schimmelcultures, Baarn, The Netherlands.

The hydroxylated steroids produced by the invention process in particularly the 7α-hydroxylated steroids can be employed as intermediates by any art recognized procedure for producing synthetic hormones, cholic acid and various pharmaceuticals. The following Examples illustrate the invention process but are not meant to limit the invention in scope or spirit. The temperatures are given in degrees Centigrade.

EXAMPLE 1

A culture medium with 1% cornsteep liquor and 1% glucose was adjusted to pH 6.5. 100 ml of this medium were sterilized at 120° for 15 minutes in a 500 ml flask with paper stopper. After cooling down, it was inoculated with the mycelium of a two weeks old malt extract-agar culture of IFO 6469. The culture was then rotary shaken at 26.5° with 180 movements per minute. After 3 days, there were added 300 mg of 4-androstene-3,17-dione which had been emulsified by exposure to ultrasonic wave for 10 minutes in 3 ml of 0.1% Tween 80 solution. The incubation was then continued for 6 days and thereafter the culture liquid was filtered off and the mycelium was washed with water, so that the end volumes of filtrate and wash-water amounted to 100 ml.

100 ml of culture filtrate were extracted three times with 100 ml of ethyl acetate each time. The combined extracts were dried over sodium sulphate and evaporated to 5 ml under reduced pressure. The concentrate was chromatographed on silicic acid (Mallinckrodt) with the use of chloroform-acetone as the elution agent. 7α-hydroxy-4-androstene-3,17-dione was eluted with chloroform-acetone (19:1) and 7α,17β-dihydroxy-4-androsten-3-one was eluted with chloroform-acetone (15:3). The homogeneous fractions were pooled and recrystallised from acetone. There were obtained 80.7 mg of 7α-hydroxy-4-androstene-3,17-dione, melting point 254.5°–256.5°, and 46.0 mg of 7α,17β-dihydroxy-4-androsten-3-one, melting point 191°–193°.

EXAMPLE 2

A fermentation medium containing 1% lactose, 3% Bacto-liver (Difco), 0.1% $KH_2PO_4$ and 0.05% KCL was adjusted to pH 6.3 and sterilized at 120° for 15 minutes. The nutrient medium was inoculated in 10 100 ml portions with the mycelium of a two weeks old malt extract-agar slant culture of IFO 6469. The cultures were then shaken on the rotary machine at 26.5° with 180 movements per minute. After 22 hours, there were added in each case 50 mg of 17α,21-dihydroxy-4-pregnene-3,20-dione (previously emulsified by exposure to ultrasonic wave for 10 minutes in 1 ml of 0.1% Tween 80), so that the concentration of steroid amounted to 0.5 mg/ml of fermentation solution. The cultures were then incubated for a further 92 hours; thereafter pooled, filtered and washed with water; so that from 1,000 ml of nutrient solution there was obtained a total volume of 1,100 ml.

The thus-obtained 1,100 ml of culture solution were extracted with ethyl acetate and concentrated to a small volume under reduced pressure. The residue was chromatographed on silicic acid with the use of chloroform-acetone as the elution agent. The homogeneous fractions were pooled and crystallized from ethyl acetate. There were obtained 188 mg of 7α,17α,21-trihydroxy-4-pregnene-3,20-dione, melting point 221.5°–223.5°.

EXAMPLE 3

100 ml of a nutrient medium, containing 1% cornsteep liquor and 1% glucose, were adjusted to pH 6.5 and, after sterilization, inoculated with the mycelium of IFO 6469. After incubation at 26.5° on the rotary shaking machine during 22 hours, 100 mg of 17β-hydroxy-4-androsten-3-one in 1 ml of dimethyl sulphoxide were added and the incubation was continued at 26.5° for a further 8 days. Thereafter, the fermentation solution was filtered, the filtrate was extracted with ethyl acetate and concentrated to a small volume and under reduced pressure. The concentrate was chromatographed on silicic acid with chloroform-acetone. There were obtained 17.9 mg of 7α,17β-dihydroxy-4-androsten-3-one.

EXAMPLE 4

100 ml of a nutrient medium containing 2% saccharose, 1% S-3 meat (Ajinomoto Co.) 1% peptone and 0.5% KH$_2$PO$_4$ was adjusted to pH 6.5, sterilized and inoculated with mycelium of Botryodiplodia malorum CBS 134.50. After two-days incubation at 26.5° on the rotary shaking machine, 50 mg of 17α,21-dihydroxy-4-pregnene-3,20-dione in 1 ml of dimethyl sulphoxide were added and the fermentation was continued at 26.5° for a further 6 days. Thereafter, the fermentation solution was collected and worked-up as in the foregoing Examples. There were obtained 8.5 mg of 7α,17α,21-trihydroxy-4-pregnene-3,20-dione.

EXAMPLE 5

100 ml of a fermentation medium, which contained 1% glucose and 1% cornsteep liquor and which had a pH of 6.5, was sterilized at 120° for 15 minutes. The medium was inoculated with the mycelium of a two weeks old malt extract-agar culture of IFO 6469. After the culture had been incubated at 26.5° for two days on a rotary shaking machine, 100 mg of 3β-hydroxy-5-androsten-17-one, dissolved in 1 ml of dimethyl sulphoxide, were added and the incubation was continued for three further days.

The culture filtrate was then extracted with 300 ml portions of ethyl acetate, the extracts dried over sodium sulphate and concentrated under reduced pressure to a small volume. The concentrate was chromatographed on a silicic (Mallinckrodt) column with chloroform-acetone. 7α-Hydroxy-4-androstene-3,17-dione was eluted with a mixture of chloroform-acetone (19:1) and 7α,17β-dihydroxy-4-androsten-3-one was eluted with chloroform-acetone (15:3). The homogeneous fractions were combined and crystallized from acetone and yielded 20 mg of 7α-hydroxy-4-androstene-3,17-dione, melting point 254°–255° C., and 10.5 mg of 7α,17β-dihydroxy-4-androsten-3-one, melting point 191°.

EXAMPLE 6

Following the procedure in Example 5 replacing 100 mg of 3β-hydroxy-5-androsten-17-one with 50 mg of 3β-hydroxy-5-pregnen-20-one, provides thereby 10.5 mg of 7α-hydroxy-4-pregnen-3,20-dione.

We claim:

1. A process for producing 7α-hydroxylated steroids comprising fermenting a 7-unsubstituted steroid selected from the group consisting of dehydroepiandrosterone, pregnenolone, and a steroid having the formula

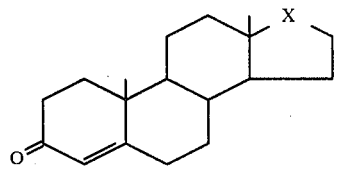

wherein X represents

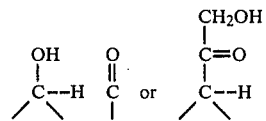

with microorganisms of IFO 6469 or Botryodiplodia malorum CBS 134.50 in a culture solution or medium until the 7-unsubstituted steroid is hydroxylated.

2. A process according to claim 1 further comprising recovering the hydroxylated steroid from the culture solution or medium.

3. A process for producing 7α-hydroxylated steroids comprising reacting a 7-unsubstituted steroid selected from the group consisting of dehydroepiandrosterone, pregnenolone and a steroid having the formula

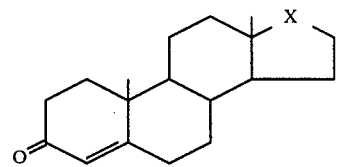

wherein X represents

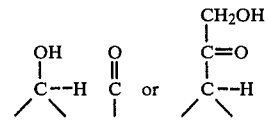

with a hydroxylating enzyme extract obtained from microorganisms of IFO 6496 or Botryodiplodia malorum CBS 134.50 in a reaction mixture until the 7-unsubstituted steroid is hydroxylated.

4. A process according to claim 3 further comprisig recovering the hydroxylated steroid from the reaction mixture.

* * * * *